United States Patent [19]
Nitzan

[11] Patent Number: 5,862,805
[45] Date of Patent: Jan. 26, 1999

[54] APPARATUS AND METHOD FOR MEASURING THE VARIABILITY OF CARDIOVASCULAR PARAMETERS

[75] Inventor: Meir Nitzan, Mizrach Benyamin, Israel

[73] Assignee: Optelmed Ltd., Israel

[21] Appl. No.: 744,816

[22] Filed: Nov. 6, 1996

[30] Foreign Application Priority Data

Nov. 16, 1995 [IT] Italy ........................................ 116020

[51] Int. Cl.⁶ .................................................. A61B 19/00
[52] U.S. Cl. ........................................... 128/898; 600/479
[58] Field of Search .................................. 128/666, 667, 128/898; 600/481, 480, 485, 479, 507

[56] References Cited

U.S. PATENT DOCUMENTS

| | | | |
|---|---|---|---|
| 3,980,075 | 9/1976 | Heule ...................................... | 128/666 |
| 4,834,107 | 5/1989 | Warner . | |
| 5,379,774 | 1/1995 | Nishimura et al. ...................... | 128/666 |
| 5,423,322 | 6/1995 | Clarke et al. ............................ | 128/672 |
| 5,632,272 | 5/1997 | Diab et al. .............................. | 128/633 |

OTHER PUBLICATIONS

Ratner et al. "Analysis of the Photoplethysmographic Signal" SPEI (1972):410–15, Dec. 1992.

Nitzan et al. "Faster Procedure for Deriving Regional Blood Flow by the Noninvasive Transient Thermal Clearance Method" Ann Biomed Engineering (21):259–62, May 1993.

Nitzan et al. "A Device for Reliable Recording of the Photoplethysmographic Signal" SPIE (2084): 171–177, Sep. 1993.

Nitzan et al. "Infrared Radiometry of Thermally Insulated Skin for the Assessment of Skin Blood Flow" SPEI 33(9): 2953–7, Sep. 1994.

Nitzan et al. "Spontaneous Low Frequency Fluctuations in Finger Blood Volume, Measured by Photoplethysmography" SPEI (2631): 84–91, Sep. 1995.

Ugnell et al. "The Time–Variable Photoplethysmographic Signal; Dependence of the Heart Synchronous Signal on Wavelength and Sample Volume" Med Eng Phys 17(8): 571–8, Dec. 1995.

Schnall et al. "A Rapid Noninvasive Blood Pressure Measurement Method for Discrete Value and Full Waveform Determination" J Applied Phys. 80(1):307–14, 1996.

*Primary Examiner*—Mickey Yu
*Assistant Examiner*—Kelly O'Hara
*Attorney, Agent, or Firm*—Rogers & Killeen

[57] ABSTRACT

Apparatus for measuring the variability of cardiovascular parameters, having a photoplethysmographic (PPG) probe, including a modulated first light source and a photodetector, a demodulator connected to the photodetector for demodulating PPG signals detected by the photodetector, an analog to digital converter for digitizing the demodulated signals, and a processor for repeatedly analysing the PPG signals for a predetermined number of times. A method for measuring the variability of cardovascular parameters.

4 Claims, 4 Drawing Sheets

APPARATUS AND METHOD FOR MEASURING THE VARIABILITY OF CARDIOVASCULAR PARAMETERS

BACKGROUND OF THE INVENTION

The present invention relates to an apparatus and method for measuring the variability of cardiovascular parameters.

The heart rate fluctuates spontaneously about its average value in several frequencies. These fluctuations are attributed to the activity of the two branches of the Autonomic Nervous System (ANS): the sympathetic and the parasympathetic nervous systems. Power spectrum analysis revealed fluctuations in three main frequency ranges: the high frequency fluctuations in the respiration rate, which are related to the parasympathetic nervous system; the mid-frequency fluctuations, which are usually related to both branches of the ANS and the low frequency fluctuations, at the rate of 0.03–0.08 Hz, which are attributed to the activity of the sympathetic nervous system.

The Heart Rate Variability (HRV) measurement provides information on the ANS function: in several pathologies the HRV pattern is abnormal. The measurement itself is simple and noninvasive and has potential to be used as a clinical tool for the assessment of pathological ANS. At present, such measurements are not used routinely because the difference between pathological and normal HRV is not well defined. The pattern of the HRV differs greatly even between normal subjects, and masks the different pattern of the pathological HRV.

During systole (heart contraction), blood is ejected from the left ventricle into the peripheral organs, thereby increasing their blood volume. The measurement of this Systolic Blood Volume Increase (SBVI) is called plethysmography. The simplest plethysmographic method is Photoplethysmography (PPG), in which light is incident on some site of the skin, so that part of it enters the tissue. That light is partly scattered and partly absorbed by the red blood cells. The light which emerges out of the skin is measured by a photodetector. The output signal shows pulsations in the heart rate, due to the variations in tissue blood volume, which occur by the heart beats.

The PPG method is not suitable for absolute evaluation of the SBVI, because the absolute value of the signal depends on the skin color, on the pressure of the probe on the skin and because the signal varies spontaneously as a function of time even during the same examination. At present, the method is used for the measurement of the heart rate (where the absolute PPG is not important) and for pulse oximetry—measurement of oxygen saturation in the arterial blood, by measuring the ratio of the PPG signal for two or three different wavelenths (where only the ratio between two wavelengths is required).

U.S. Pat. No. 4,834,107 discloses a system which, in some respects, is similar to the present invention. In that patent, the PPG signal of one, single pulse, is digitally analyzed, in order to determine the systolic, diastolic and mean blood pressure and the pulse pressure.

SUMMARY OF THE INVENTION

In accordance with the present invention, however, no blood pressure value is derived from the PPG signal. Furthermore, the parameter which is derived, the degree of the variability of the PPG parameter or the maximal correlation coefficient between two PPG parameters or between the values of the same PPG parameter in two sites of the body and the lag between them, cannot be derived from a single pulse, but from a series of more than e.g., 30 pulses, in order to detect the low frequency sympathetic nervous system regulated fluctuations.

It is therefore a broad object of the present invention to overcome the above-mentioned and other drawbacks of the known methods for SBVI analysis and to provide a system and a method facilitating improved evaluation of the fluctuations in SBVI and other cardiovascular parameters.

In accordance with the present invention there is provided an apparatus for measuring the variability of cardiovascular parameters, comprising at least one photoplethysmographic (PPG) probe, each probe having a modulated first light source and a photodetector, a demodulator connected to said photodetector for demodulating PPG signals detected by said photodetector, an analog to digital converter for digitizing the demodulated signals, and a processor for repeatedly analysing said PPG signals for a predetermined number of times.

The invention further provides a method for measuring variability of cardiovascular parameters, comprising performing a series of PPG measurement on a patient over a predetermined period of time, selecting parameters to be analyzed for a group of parameters including the blood volume (BV) of the measured tissue; the amplitude (AM) of the systolic increase in the blood volume of the tissue and the time duration (P) between the maxima of two adjacent PPG pulses and the maximal rate of increase (Vmax) of the blood volume, and measuring the standard deviation of each parameter.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE PREFERRED EMBODIMENTS

Figure 1:
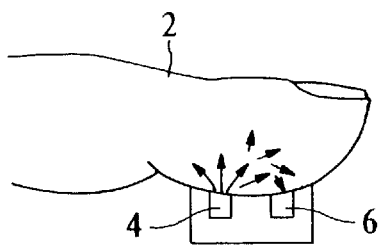
FIG. 1 illustrates a known technique for effecting PPG measurements.

There is illustrated in FIG. 1 the known PPG measurement effected on a patient's finger 2 by the application thereto of a light source 4 and a light detector 6. The PPG can be measured either by transmission of light through the tissue or by reflection from the skin.

Figure 2:
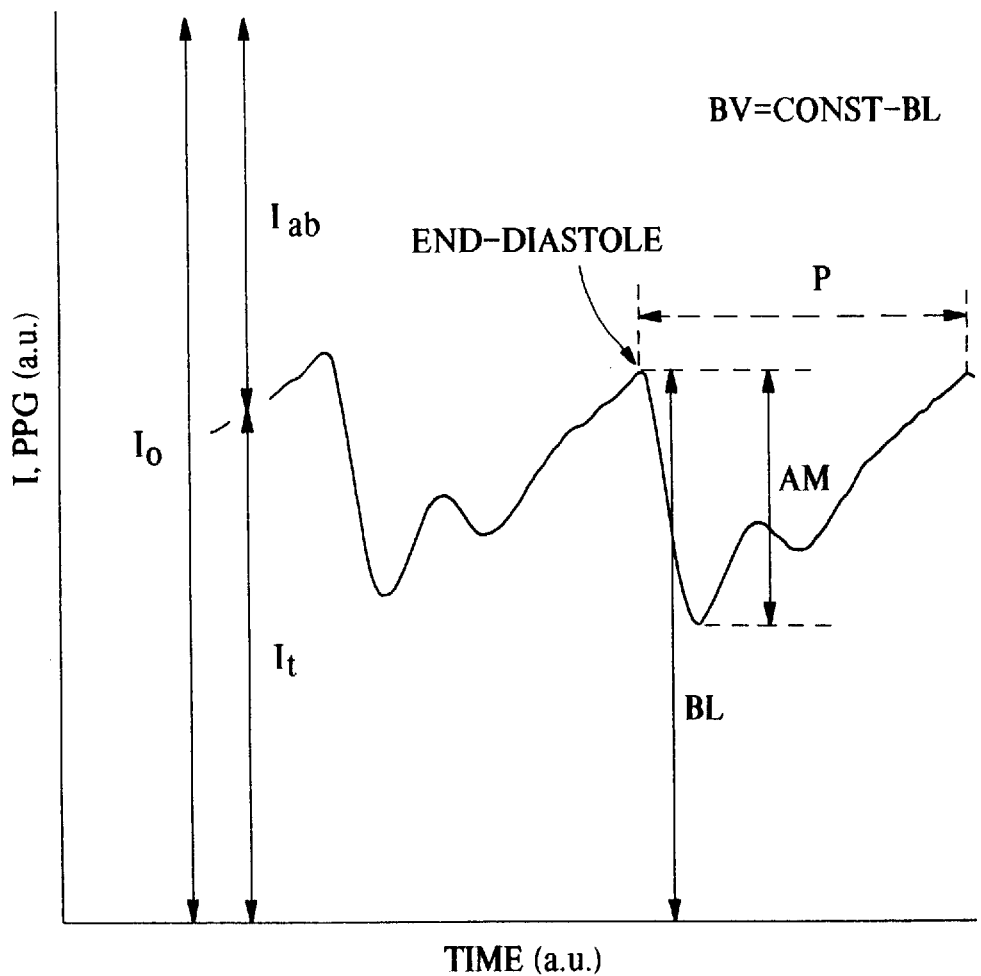
FIG. 2 illustrates a PPG signal obtained by the measurements effected by the technique of FIG. 1.

The PPG signal obtained by the above-described measurement is shown in FIG. 2. Several parameters which can be derived from the pulse are also depicted on the curve:

1. The baseline (BL), which is inversely related to the tissue blood volume: higher blood volume results in higher absorption of the light and lower output signal. The parameter, BV defined by BV=Const.−BL is therefore a parameter which is directly related to the blood volume in the tissue under investigation.

2. The amplitude (AM) of the PPG signal, which is related to the SBVI. SBVI depends on the compliance to pressure of the blood vessels: higher rigidity of the vessels reduces their volume change during systole, while higher elasticity enables higher dilation during the systolic period.

3. The PPG pulse period P is actually the cardiac beating period, and its variability is therefore the classical HRV.

The PPG signal illustrated in FIG. 2 was measured for several hundred pulses and the three parameters BV, AM and P were derived for each pulse.

Figure 3:
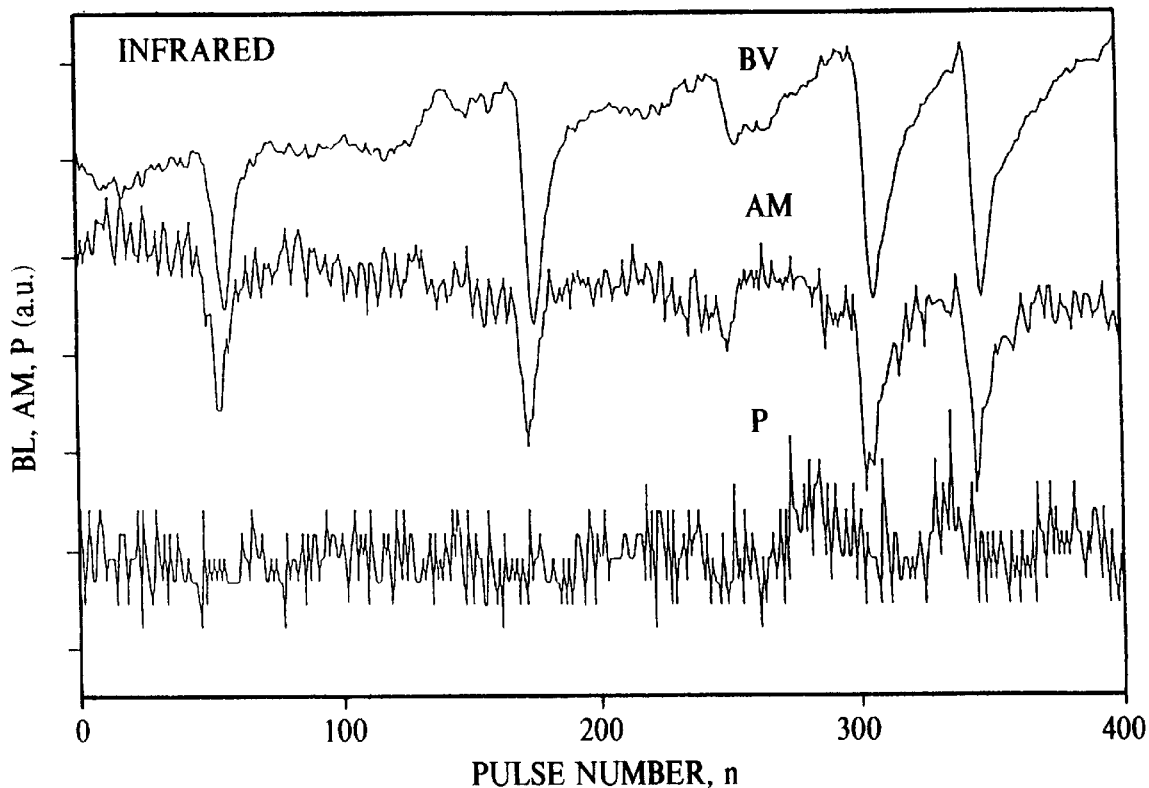
FIG. 3 illustrates a signal curve showing the dependency of the parameters on the pulse number.
Figure 4:
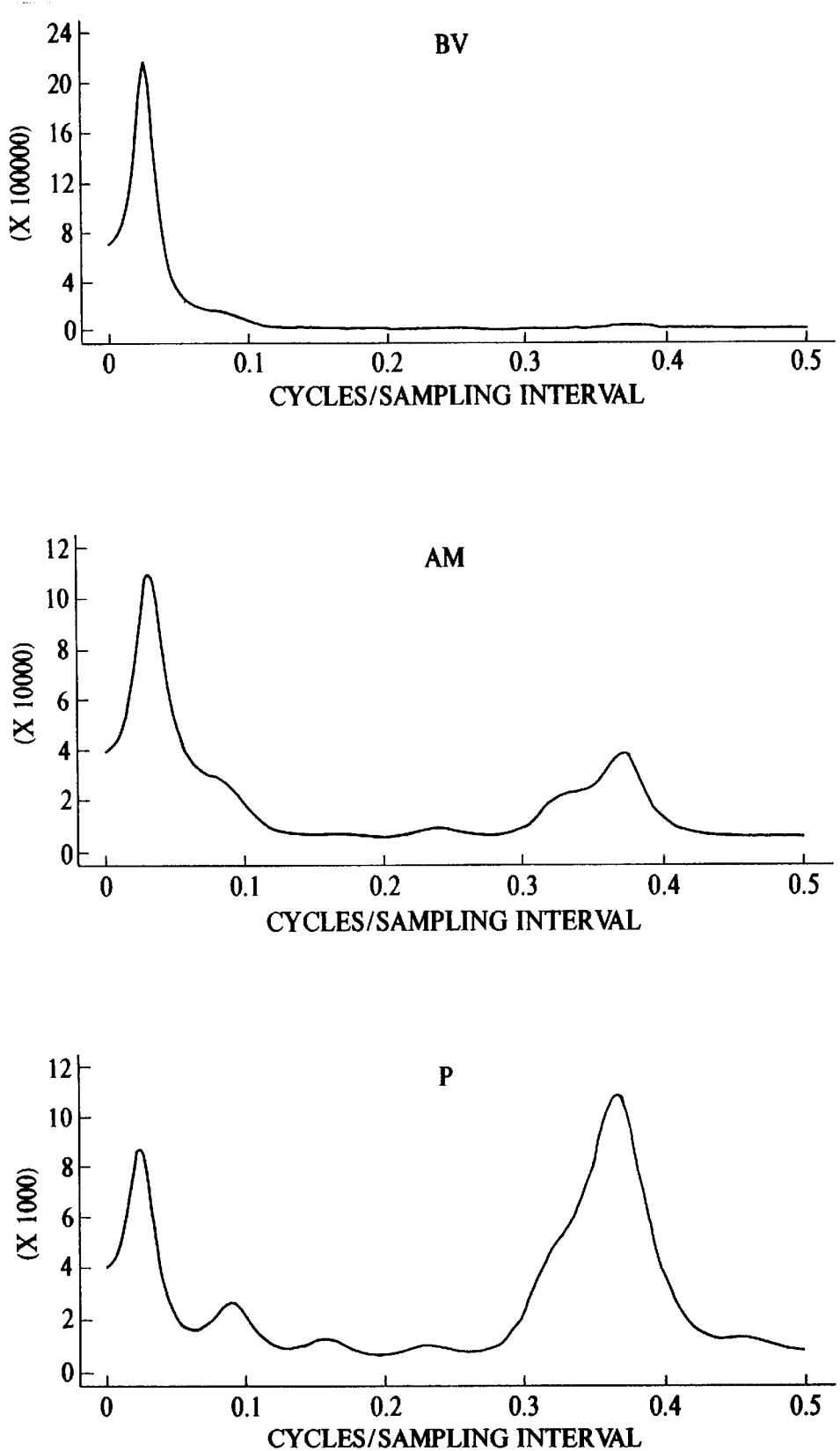
FIG. 4 is a power spectrum of the dependency of the parameters of FIG. 3, on time.

Shown in FIG. 3 is the dependence of each parameter on the pulse number. The power spectrum of the dependence on time of the three parameters BV, AM and P was then computed and the three spectra obtained for one of the subjects are shown in FIG. 4. It can be seen that all three parameters fluctuate in the three frequencies mentioned above, but the intensities of the fluctuations in the different frequencies differ between BV, AM and P: the high frequency fluctuations dominate the P curve, while the low frequency fluctuations are more prominent in the BV and AM curves.

It was found that neurologic pathologies result in difference in the BV and AM variability pattern, in accordance with the results obtained for HRV examinations. The changes in the low frequency are better seen and measured in the BV and AM curves, probably due to the direct effect of the smypathetic nervous system on the diameter of the blood vessels, changing thereby their volume and compliance. It is therefore expected that pathologies in the sympathetic nervous system, which dominate the low frequency fluctuations, will be better diagnosed by the PPG measurement through the analysis of the dependence of the PPG parameters on time.

Figure 5:
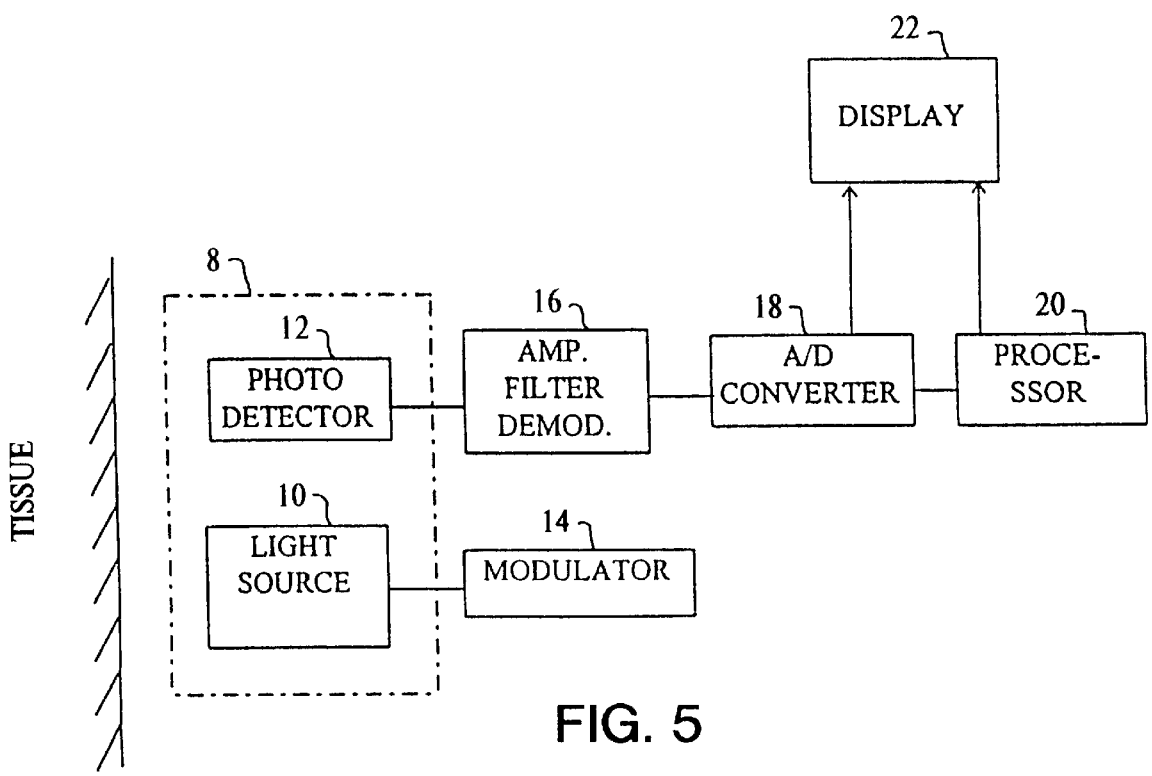
FIG. 5 is a block diagram of the system according to the present invention.

In the preferred embodiment shown in FIG. 5, there is seen the PPG system arranged to reliably measure the variability of several parameters of the PPG signal, such as, the baseline BL, (or BV which is equal to a Const.−BL), the amplitude AM, the period P, the maximal rate of increase Vmax of the tissue blood volume, and the time duration T from the maximum to the minimum. As explained above, BV is related to the tissue blood volume, AM is related to the blood vessels' elasticity and P is the cardiac cycle period. Vmax is related to the maximal contraction rate of the left ventricle, and is influenced by several cardiac and peripheral vascular parameters.

The system comprises one or more PPG probes 8, each includes either one light source 10 or two light sources of different wavelengths, and a photodetector 12. The light intensity is modulated by modulator 14 and the detected PPG signal is amplified, and filtered in order to avoid background light, and then demodulated in circuit 16. The demodulated signal then digitized in the A/D converter 18 and the digitized signal is analyzed either by a microprocessor 20 or by computer, in order to obtain, for each pulse, the desired parameters, BV, AM, P, Vmax and T. A display 22 is used for displaying either the PPG signal or the curves of the different parameters as a function of the pulse number. When the measurement is performed in two sites, the correlation function can also be shown on the display.

In order to reliably measure the above-mentioned parameters the electronic components should be accurately designed. RC filtration of the high DC component of the PPG signal is not allowed, since it may significantly modify the other parameters. The discrimination between the DC and the AC components of the PPG signal (BL and AM, respectively) should therefore, be done digitially, using an A/D convertor of high resolution.

The preferred site of measurement is the fingertip, since the fingertip blood vessels are highly inervated by the symphathetic nervous system. Other sites on the body can also be used for the examination, such as the forearm, toe, leg or earlobe.

The examination of the PPG parameters variability can also be performed on different sites of the body, such as different fingertips of the same hand or on different hands, on fingers and toes, or on fingers and forearm. The different curves from the different sites can then be compared in order to detect pathological or physiological changes between the different sites.

The analysis of the PPG parameters may include:

1. Automatic derivation of the above parameters for each pulse signal as described with reference to FIG. 2. For that task the minimum and the maximum for each pulse is determined in order to derive BL, AM, P and T, and the derivative of the PPG curve is calcualated in order to obtain the maximal rate of increase of the blood volume;

2. Plottings of each parameter vs. time curve in order to check that the automatic analysis was properly performed;

3. Power spectrum analysis of each parameter;

4. Cross correlation (CC) analysis for each desired pair of these parameters, e.g., $P_1$ and $P_2$, according to the well known formula for CC:

$$CC(\tau) = \int_{-\infty}^{+\infty} P_1(t)P_2(t-\tau)dt.$$

CC provides information on the degree of correlation between the two parameters, $P_1$ and $P_2$. CC is function of the parameter $\tau$, the lag between $P_1$ and $P_2$. The CC curve is displayed and two parameters are derived therefrom: the maximal correlation coefficient and the lag $\tau$ required for obtaining that maximal correlation.

Figure 6:
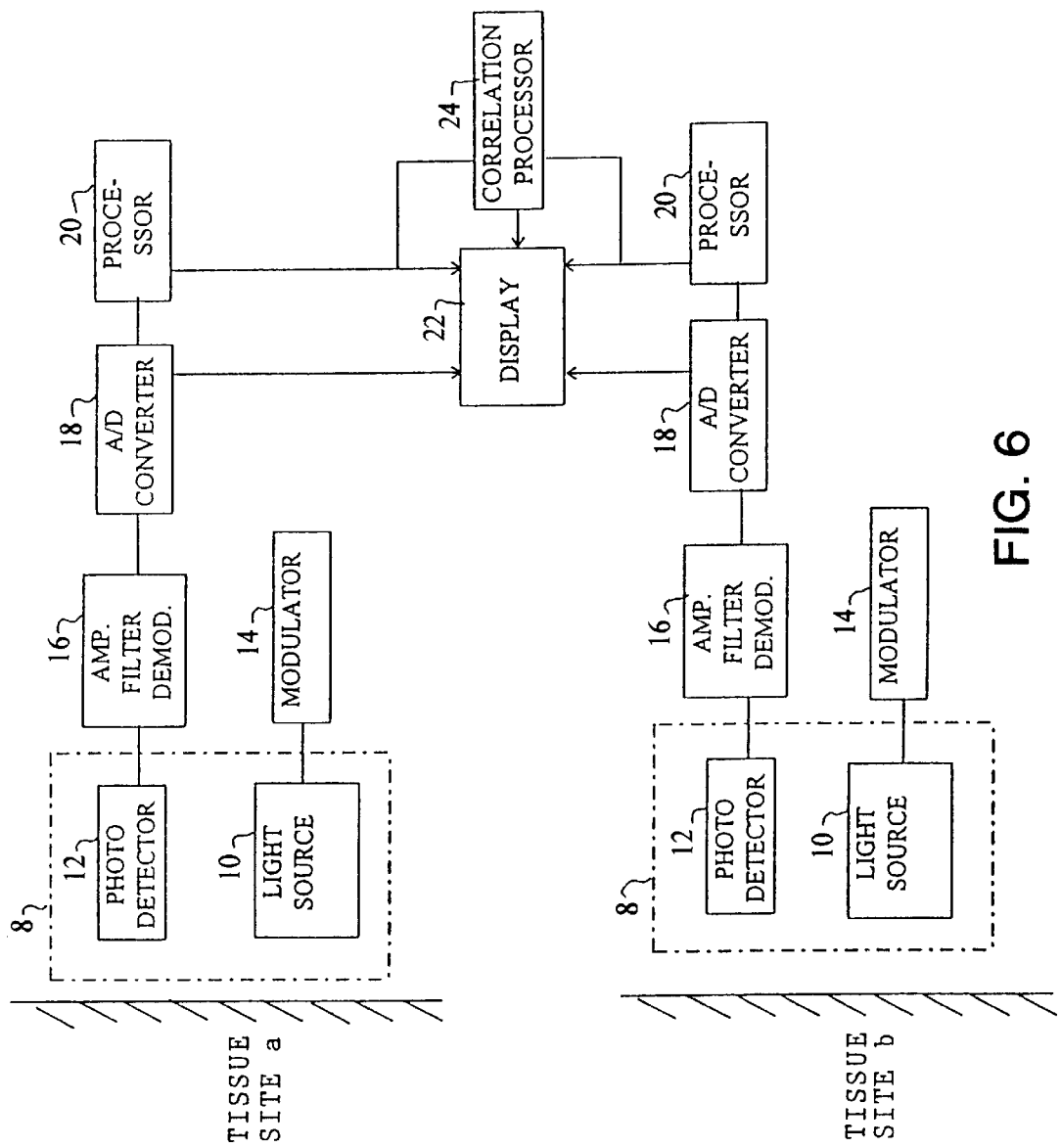
FIG. 6 is a block diagram of a system for performing measurements at two sites on a body.

The examination of the PPG parameters' variability can also be performed on different sites of the body, such as different fingertips of the same hand or on different hands, on fingers and toes, or on fingers and forearm. As illustrated in FIG. 6, for each PPG parameter, the curves describing the value of the parameter as a function of the pulse number can be obtained for each site of measurement and the parameter dependence on time for the different sites can be compared. A correlation processor 24 can advantageously be connected between the processors 20 of each of the probes.

One of the methods for detecting pathological changes between the different sites is the use of the correlation function $$CC(\tau) = \int_{-\infty}^{+\infty} P_a(t)P_b(t-\tau)dt.$$

where $P_a(t)$ and $P_b(t)$ are the corresponding values of the same parameter in the two different sites, a and b. As an example, the correlation coefficient $CC(\tau=0)$ between two fingers in different hands for normal subjects is above 0.90. Lower values indicate lower coordination between the two sites.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for measuring variability of cardiovascular parameters, comprising:

performing a series of photoplethsymographic measurement on a patient over a predetermined period of time;

selecting parameters to be analyzed from the group of parameters consisting of: the blood volume (BV) of the measured tissue; the amplitude (AM) of the systolic increase in the blood volume of the tissue and the time duration (T) between the maxima of two adjacent photoplethsymographic pulses and the maximal rate of increase (Vmax) of the blood volume, and measuring the standard deviation of any selected parameter from said parameters.

2. The method as claimed in claim 1, further comprising performing correlation between the values of a selected parameter of two different sites on the body of said patient.

3. The method as claimed in claim 2, wherein said correlation is performed for each selected parameter P by the formula $$CC(\tau)=P_a(\tau)P_b(t-\tau)dt$$

where $CC(\tau)$ is the cross correlation which depends on the time lag between two parameters $P_a$ and $P_b$; $P_a(\tau)$ and $P_b(\tau)$ are the corresponding values of the same parameter in the two different sites, a and b, at a time t, and $\tau$ is time lag.

4. A method as claimed in claim 1, further comprising the step of displaying curves depicting variations of the selected parameters as a function of time.

* * * * *